United States Patent [19]

Rambo et al.

[11] Patent Number: 5,010,902
[45] Date of Patent: Apr. 30, 1991

[54] COMPRESSION ORB

[75] Inventors: Robert D. Rambo, Sellersville, Pa.; John A. Yorke, Canastota, N.Y.

[73] Assignee: Ace Medical Inc., Sellersville, Pa.

[21] Appl. No.: 554,349

[22] Filed: Jul. 19, 1990

[51] Int. Cl.$^5$ .............................. A61F 5/30; A61F 5/34
[52] U.S. Cl. ..................................... 128/888; 128/889; 128/846; 128/DIG. 22; 128/112.1; 128/115.1; 606/201; 606/204
[58] Field of Search ............... 128/DIG. 22, 846, 887, 128/888, 112, 113, 114, 115, 117, 120; 606/201, 202, 203, 204

[56] References Cited

U.S. PATENT DOCUMENTS

| | | | |
|---|---|---|---|
| 1,426,124 | 8/1922 | Thomas | 128/117.1 |
| 1,607,208 | 11/1926 | Pease | 128/113.1 |
| 2,367,690 | 1/1945 | Purdy | 128/888 |
| 3,265,064 | 8/1966 | Gruber | 128/117.1 X |
| 4,182,338 | 1/1980 | Stanulis | 606/203 |
| 4,829,994 | 5/1989 | Kurth | 606/203 X |

Primary Examiner—Robert A. Hafer
Assistant Examiner—Brian E. Hanlon
Attorney, Agent, or Firm—Katherine McGuire

[57] ABSTRACT

A compression orb for use in combination with known bandage means to simulate manual digital pressure hemostasis following an arterial or venous puncture. The orb is formed from transparent plastic and is shaped as a hollow dome having a central, raised bulb or second, smaller dome which is integrally formed with and extends from the first domed portion. The flat, circular surface of the orb is releasably attached to the bandage means and the raised bulb portion of the orb is pressed upon the puncture site by means of the secured bandage. The bandage means includes a transparent window through which the orb and puncture site may be viewed without having to lift the bandage and orb from the wound to check for bleeding.

3 Claims, 2 Drawing Sheets

COMPRESSION ORB

BACKGROUND OF THE INVENTION

This invention relates to devices used to stop bleeding from an arterial or venous puncture site on the human body and, more particularly, to a uniquely configured compression orb which is used in combination with any of a variety of available, known bandage means which secure the orb in the proper position on the puncture site to simulate manual digital pressure hemostasis.

Certain medical procedures require the insertion of a needle into the artery or vein of the patient, either momentarily to inject or withdraw fluids to and from the blood stream, respectively, or for extended periods of time, such as is required for dialysis and transfusion treatments, for example. Withdrawal of the needle from the artery or vein requires immediate digital pressure application to the puncture site to stanch the bloodflow therefrom. The pressure must be applied for a period of time sufficient to allow the blood to clot and seal the puncture wound by way of the body's own natural healing process.

This routine is typically performed by trained medical personnel who use their fingers and hands to apply the needed pressure. Devices have been developed to simulate the required manual digital pressure hemostasis such that the medical attendant may be available for other needed duties. For example, as seen in U.S. Pat. No. 4,829,994, issued to Kurth on May 16, 1989, a pelvic apron including a groin strap is provided which secures what Kurth terms a shaped mass or "pellet" 24 (FIG. 6) in position over an incision in the femoral artery following catheterization of the patient. The pellet provides directed pressure upon the incision site by virtue of the uniquely configured pelvic apron piece and groin strap which, when wrapped about the body as seen in FIGS. 3, 4 and 5, secures and presses the pellet over the incision point to thus stanch the blood flow therefrom until the artery repairs itself by the natural clotting action of the blood. The pellet 24 used by Kurth in combination with his pelvic apron and groin strap is the same pellet disclosed in the Colapinto compression device which is shown as prior art in FIGS. 1 and 2 and described at lines 29-40 in column 2 of the Kurth specification. Kurth's description of the shape of the pellet, i.e., "a sector of a sphere with a flattened pole" and statement that it "serves to replace the equivalent amount of folded gauze to define the pressure point against the femoral arterial or venous incision" reveal the inadequacies of such a pellet for the intended purpose. In particular, as seen in FIG. 5 of Kurth, the skin contacting surface of pellet 24 contacts the incision point at artery 60 as well as a significant skin area immediately adjacent artery 60. The large surface area of pellet 24 which contacts the skin distributes the downward force created by the pelvic apron and groin strap over an equal amount of skin surface. Since the diameter of the pellet is stated to be approximately 2⅛" (column 2, line 33), the skin area onto which the downward force is distributed can be said to comprise a circle having a diameter of approximately 2⅛" with the incision site at artery 60 being at the center of the circle. This distribution of force over the surrounding area of the incision site requires that a significant amount of pressure be applied to the pellet by the pelvic apron and groin strap such that the pellet may stop the bleeding from artery 60. Even with such a strong pressure applied to pellet 24, artery 60 may take a significant period of time to heal due to a lack of a focalized pressure directly aimed at the artery.

U.S. Pat. No. 4,182,338, issued to Stanulus on Jan. 8, 1980, discloses a pressure appliance 10 having a truncated, pyramid-shaped body having a cylindrical pressure applicator 16. Although the pressure appliance of the '338 patent attempts to provide a localized pressure point for the punctured artery, the blunt shape of the pressure applicator 16 disposed upon the flat surface 12 of the appliance 10 fails to effectively direct pressure to the artery itself. Instead, the downward force of applicator 16 and surface 12 applied by securing straps 20 and 22 is distributed in the area of the skin surrounding the artery or vein. The skin-contacting surfaces of applicator 16 and surface 12 lie in spaced, parallel planes whereby any pressure directed toward the skin of the body is distributed over an area of skin equaling the dimensions of rectangular surface 12, with the blunt end of applicator 16 further indenting the skin an equal distance along all points defined by the surface of applicator 16's blunt end. The artery in this instance is thus receiving the same amount of pressure as is the surrounding area of skin contacted by the blunt end of applicator 16 and, to a slightly lesser extent, the surrounding area of skin contacted by surface 12 is receiving the same amount of pressure.

It is thus a main object of the present invention to provide a compression orb for use in combination with appropriate bandage means which is effective in applying a directed force to an arterial or venous puncture site such that manual digital pressure hemostasis is simulated.

It is a further object to provide an arterial or venous puncture compression device which directs and focuses pressure upon the arterial or venous puncture site such that bleeding therefrom is stanched while normal systemic arterial pressure is maintained.

It is another object of the present invention to provide an arterial or venous puncture compression orb which includes means to allow visual inspection of the puncture site which obviates the need for trained medical personnel to periodically lift the device to inspect the puncture site for bleeding.

Other objects will in part be obvious and in part appear hereinafter.

SUMMARY OF THE INVENTION

In accordance with the foregoing objects, there is provided a compression orb for use in combination with known bandage means which, when applied to an arterial or venous puncture site, simulates manual digital pressure hemostasis. The orb is configured in the shape of a dome and includes a raised bulb in the shape of a second, smaller dome at the center of the orb. The raised bulb serves to direct and focus pressure upon the arterial or venous puncture site when the orb and bandage means are applied to the body in the manner to be described more fully hereinafter.

In the preferred embodiment, the orb is constructed of a clear, hard plastic such that the puncture site is visible when the orb is pressed thereupon. The orb securing bandage means includes a transparent "window" which is placed in superposed relation over the transparent orb such that visual inspection of the puncture site is possible by looking through the bandage window and the orb without having to lift the bandage and orb from the body.

DETAILED DESCRIPTION

Figure 1:
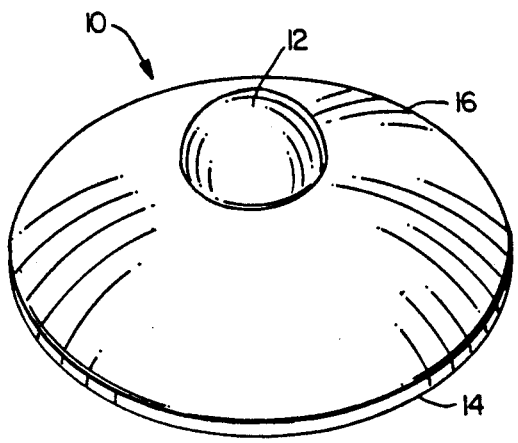
FIG. 1 is a top perspective view of the compression orb.

Referring now to the drawings, there is seen in the various Figures the compression orb of the invention denoted generally by the reference numeral 10. As seen, orb 10 is configured in the shape of a dome having a raised bulb 12 at its center. More specifically, orb 10 has a circular base 14 with integral sides extending in the same direction therefrom which taper gradually inwardly toward the center axis of base 14 to form a first domed surface 16. A second domed surface or raised bulb 12 is formed at the center of orb 10 on surface 16 such that the center of bulb 12 is positioned at the central axis of base 14.

Figure 3:
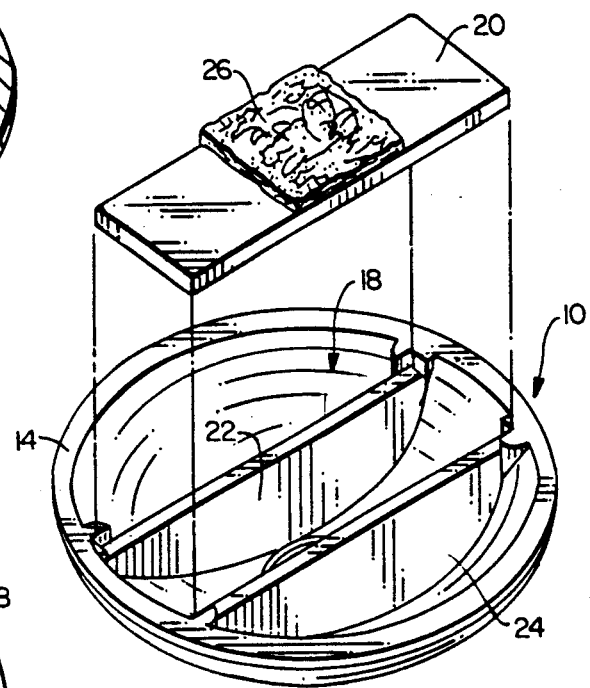
FIG. 3 is a bottom perspective view of the orb showing the orb bandage attachment means in exploded relation thereto.
Figure 2:
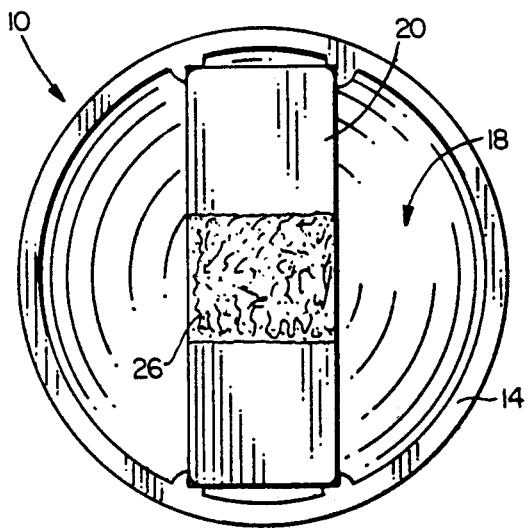
FIG. 2 is a bottom plan view of the compression orb.

Referring to FIGS. 2 and 3, it may be seen that orb 10 is molded or formed hollow, having an internal cavity 18. Bulb 12 is also hollow although bulb 12's internal cavity is not seen in the drawings. Rectilinear shaped member 20 is disposed upon the free edges of internal support flanges 22 and 24 and fixedly attached thereto. A Velcro pile segment 26 is attached to the external surface of member 20 such that orb 10 may be affixed to bandage means having respective Velcro hook segment 28, such as flexible bandage 30 seen in FIG. 5 and in phantom in FIG. 4. Bandage 30 includes two free ends having securing means 32 (e.g. velcro) such that bandage 30 may be wrapped and secured around a limb, for example, such as arm 33 seen in FIGS. 4 and 5. It is noted that orb 10 can be used at any venous or arterial puncture site on the body and include appropriate bandage means to secure orb 10 to the particular place on the body. With orb 10 affixed to bandage 30 as described above, bulb 12 is positioned directly over the arterial or venous puncture site 34. The proper amount of pressure is then applied by securing bandage 30 about arm 33. The tightness of the bandage is typically adjustable and normal systemic arterial pressure should be maintained while the bloodflow from the artery or vein puncture site 34 is stanched.

Figure 4:
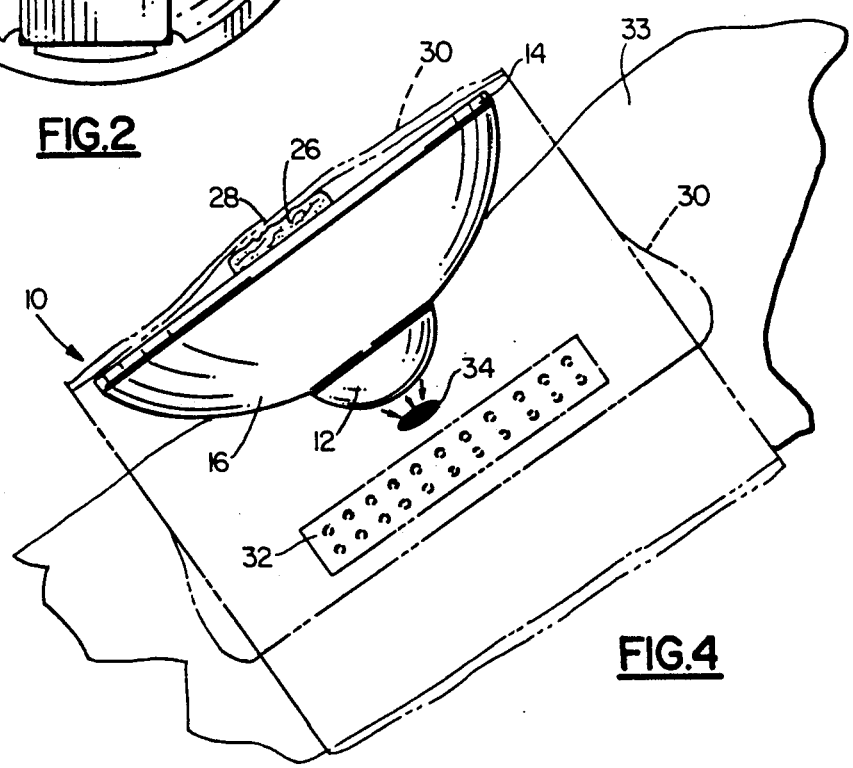
FIG. 4 is a side elevational view of the orb immediately preceeding application to the puncture site of a part of the human body.

It can thus be seen that the double-dome configuration of orb 10 creates a centralized focal point in accordance with the directional arrows of FIG. 4 not achieved with prior pressure applicators. As a result, less pressure may be applied to orb 10 while achieving satisfactory results than was possible with pressure applicators such as seen in the Kurth and Stanulus patents. The pressure of orb 10 created by bandage 30 upon puncture site 34 creates a focalized force upon the punctured artery or vein which effectively seals the wound until normal clotting can take place. In this way, the desired effect of manual digital hemostasis is simulated thereby freeing trained medical personnel for more pressing duties.

Figure 5:
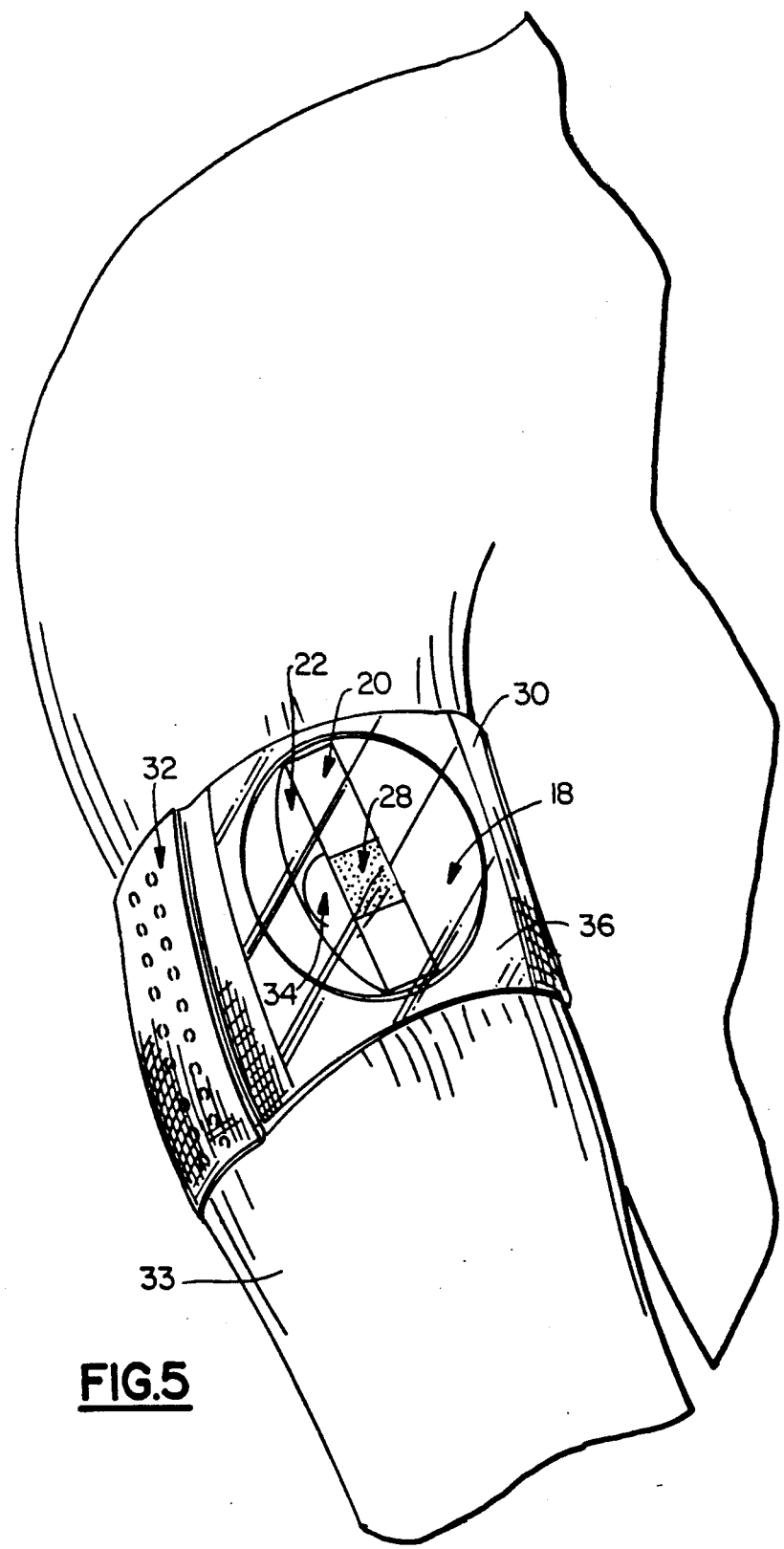
FIG. 5 is a perspective, cut-away view of the transparent orb secured in position over an arterial puncture site on the arm by a bandage including a transparent window in superposed, covering relation thereto.

A seen more clearly in FIG. 5, it is prefered that orb 10 be formed of a transparent plastic and that the bandage means 30 include a transparent window 36 which is placed in superposed relation to orb 10 upon arm 33. As seen, window 36 may comprise a piece of flexible, transparent material which is of approximately the same or larger dimensions of orb 10. The material comprising window 36 may be sewn or otherwise incorporated into bandage 30 by known means. Accordingly, when bandage 30 having window 36 is secured about transparent orb 10, immediate visual inspection of puncture wound 34 is allowed without the need to unwrap bandage 30 and lift orb 10 from the body to determine if clotting has yet occurred.

What is claimed is:

1. A compression orb for use in combination with flexible bandage means for application and securement of said orb to an arterial or venous puncture site to simulate manual digital pressure hemostasis, said orb comprising:
    (a) a circular base having a substantially flat bandage contacting surface including means for attachment to said bandage means;
    (b) a first domed surface integrally extending from the side of said base opposite said bandage contacting surface, said first domed surface having an internal, concave surface; and
    (c) a second domed surface integrally formed and raised from said first domed surface wherein the center of said second domed surface is concentric with said first domed surface and said circular base and wherein said orb is formed as a hollow piece.

2. A compression orb for use in combination with flexible bandage means for application and securement of said orb to an arterial or venous puncture site to simulate manual digital pressure hemostasis, said orb comprising:
    (a) a circular base having a substantially flat bandage contacting surface including means for attachment to said bandage means;
    (b) a first domed surface integrally extending from the side of said base opposite said bandage contacting surface, said first domed surface having an internal, concave surface;
    (c) a second domed surface integrally formed and raised from said first domed surface wherein the center of said second domed surface is concentric with said first domed surface and said circular base; and
    (d) a pair of parallel, spaced flanges integrally extending from and along the internal, concave surface of said first domed surface on either side of said second domed surface, the free edges of said flanges coplanar with said circular base.

3. The invention according to claim 2 wherein said bandage contacting surface is rectilinear and the two longest edges of said surface are fixedly attached to said free edges of said flanges.

* * * * *